United States Patent [19]

Hazard

[11] Patent Number: 4,701,129

[45] Date of Patent: Oct. 20, 1987

[54] FACE SHIELD DEVICE

[76] Inventor: James T. Hazard, 311 Fairmeade Rd., Louisville, Ky. 40207

[21] Appl. No.: 842,824

[22] Filed: Mar. 24, 1986

[51] Int. Cl.[4] .............................................. A61C 5/14
[52] U.S. Cl. .................................... 433/136; 433/229; 250/515.1
[58] Field of Search ........................ 433/136, 137, 229; 2/2.5, 49 R, 49 A; 128/132 R; 248/444; 250/515.1

[56] References Cited

U.S. PATENT DOCUMENTS

| | | | |
|---|---|---|---|
| 234,460 | 11/1880 | Daugherty | 248/444 |
| 372,496 | 11/1887 | Small | 248/444 |
| 607,496 | 7/1898 | Watson | 248/444 |
| 628,923 | 7/1899 | Carmichael | 433/137 |
| 2,863,256 | 12/1958 | Hegarty | 248/444 |
| 3,707,004 | 12/1972 | Kapitan et al. | 2/2.5 |
| 4,286,170 | 8/1981 | Moti | 250/515.1 |

FOREIGN PATENT DOCUMENTS

| | | | |
|---|---|---|---|
| 2442881 | 9/1974 | Fed. Rep. of Germany | 2/2.5 |
| 0126198 | 6/1959 | U.S.S.R. | 128/132 R |

Primary Examiner—John J. Wilson
Assistant Examiner—Adriene J. Lepiane
Attorney, Agent, or Firm—Charles G. Lamb

[57] ABSTRACT

A face shield device for protecting the wearer's eyes and face from debris, bacteria, and the like includes a transparent face shielding panel and a support for holding the face shielding panel in front of and spaced outwardly away from the wearer's face. The support is attached to the face shielding panel and lays on the wearer's chest. In one embodiment, the support is suspended from the wearer's neck by a flexible band which fits around the wearer's neck. In another embodiment, the support is suspended from the wearer's shoulders by shoulder engaging hook members. The face shield device may also include means to protect the wearer from ultra-violet radiation or other types of radiation harmful to the face and eyes.

14 Claims, 5 Drawing Figures

FACE SHIELD DEVICE

BACKGROUND OF THE INVENTION

The present invention relates to face and eye protectors or shields, and more particularly to a face and eye shield which is supported at the wearer's chest and extends in front of and spaced outwardly away from the wearer's face.

In the last few years there has developed a lot of interest in the dental profession of the transfer of bacteria from patient to dentist. This is caused predominantly because dentists are subjected to debris from a patients mouth while working on the patient. This debris comprises particles of tooth, filling material, water, and air borne particles coming from the oral cavity.

Moreover, there are new processes for repairing teeth which require the use of ultra violet radiation. In the use of equipment which emits this radiation, the eyes of the dentist or their assistant is subjected to this radiation which is harmful to the eyes.

SUMMARY OF THE INVENTION

It is an object of the present invention to protect the wearer's face and eyes from debris.

It is another objective of the present invention to provide a face and eye shield of the class described which will not hinder the wearer's vision and freedom of movement.

It is a further objective of the present invention to provide a face and eye shield of the class described which is comfortable to wear.

Other objectives will become apparent to those skilled in the art upon reading the disclosure set forth hereinafter.

More particularly, the present invention provides a face and eye shield device comprising a transparent face and eye shielding panel, and means supporting the face shielding panel at the wearer's chest and holding the face shielding panel in front of and spaced outwardly from the wearer's face.

BRIEF DESCRIPTION OF THE DRAWINGS

The present invention will become even more clear upon reference to the following description in conjunction with the accompanying drawings in which like numbers refer to like parts throughout the several views and wherein.

DETAILED DESCRIPTION OF THE PREFERRED EMBODIMENTS

Figure 1:
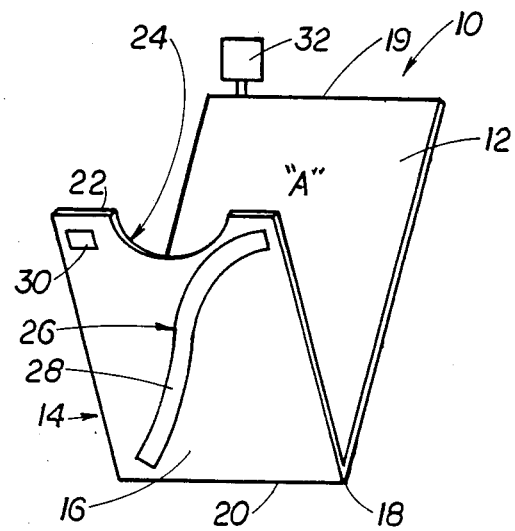
FIG. 1 is a perspective view of one embodiment of the present invention.
Figure 5:
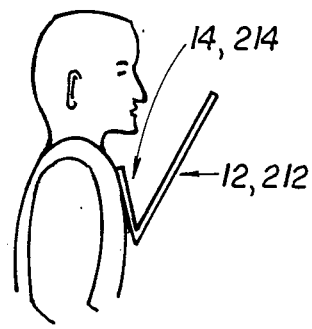
FIG. 5 is a side view depicting a person wearing any of the embodiments of FIGS. 1–4.

With reference to FIG. 1, there is shown a face and eye shield device 10 of the present invention. As shown, the face and eye shield device, generally denoted as the numeral 10, includes a transparent face shielding panel 12 and support means, generally denoted as the numeral 14, for supporting the face shielding panel 12 at the wearer's chest and holding the face shielding panel 12 in front of and spaced outwardly from the wearer's face as shown in FIG. 5.

The supporting means 14 is illustrated as a support panel 16 adapted to lay on the wearer's chest, and the support panel 16 is structurally associated with the face shielding panel 12. More particularly, the shielding panel 12 and the face supporting panel 16 are joined together at their lower edges 18 and 20, respectively. Preferably, the face shielding panel 12 and supporting panel 16 are formed of a single sheet of transparent material which is folded at the bottom edge 18 of the shielding panel 12 and bottom edge 20 of the supporting panel 16. The supporting panel 16 and face shielding panel 12 cooperate to define an acute included angle "A" therebetween with the apex of the angle being the lower painted edges 18 and 20 of the face shielding panel 12 and supporting panel 16.

Generally, the face shield panel 12 has a larger height dimension measured from the lower edge 18 to the top edge 19 than the height dimension of the supporting panel 16 measured from the lower edge 20 to the top edge 22. And, in one embodiment the top edge 22 of the supporting panel 16 is formed with a centrally located notched out area 24 configured and sized to receive therein the wearer's throat.

The face and eye shield device 10 further includes means, generally denoted as the numeral 26, for suspending the face shield device 10 from the wearer's neck. As shown, the suspending means 26 is a flexible neck band or belt 28 connected to the supporting panel 16 proximate the top edge 22 of the supporting panel 16 adopted to fit around the wearer's neck. Toward this objective the flexible neck band 28 is attached at one end to the chest contact surface of the supporting panel 16 next to one side of the throat receiving notch 24. A neck band fastener 30 is attached to the chest contact surface of the supporting panel 16 next to the other side of the throat receiving notch 24. The free end of the neck bank 28 can be adjustably connected to the fastener 30 when the neck band 28 has been located across the wearer's neck. Virtually any conventional or otherwise convenient fastener can be used. One contemplated type fastener is formed of "velcro".

As an optional feature, for example, an X-ray slide holder 32 may be attached to the top edge 19 of the face shielding panel 12 to one end of the shielding panel top edge 32 so that it will not obstruct the wearer's straight ahead vision, but will be conveniently positioned for viewing by the wearer merely glancing upwardly and to one side. Other features may include measuring devices incorporated on the shield, and means to prevent other types of radiation from penetrating through the shield, such as those emitted from laser beams and the like.

Figure 2:
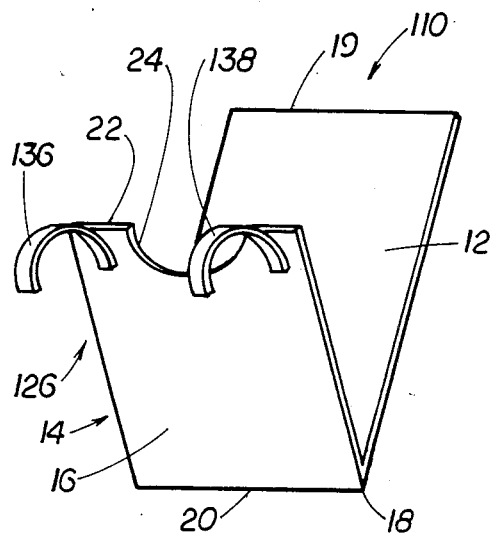
FIG. 2 is a perspective view of another embodiment of the present invention.

With reference to FIG. 2, there is shown a somewhat different embodiment of a face and eye shield device, generally denoted as the numeral 110, of the present invention. The face and eye shield device 110 is identical to the face and eye shield 10 of FIG. 1 in every respect except for the suspending means, generally denoted as the numeral 126. Therefore, all features in common with the face and eye shield 10 are denoted by the same numerals, and for the sake of brevity the description of these common features will not be repeated.

The suspending means 126 of the face and eye shield device 110 suspends the face and eye shield device 110 from the wearer's shoulders. Toward this objective, the suspending means 126 comprises a pair of spaced apart shoulder engaging hook members 136 and 138 attached to the supporting panel 16 proximate the top edge 22 to either side of the throat receiving notched out area 24. The engaging hook members 136 and 138 open downwardly and are sized, configured and spaced apart by an appropriate distance to comfortably receive the wearer's shoulders.

Figure 3:
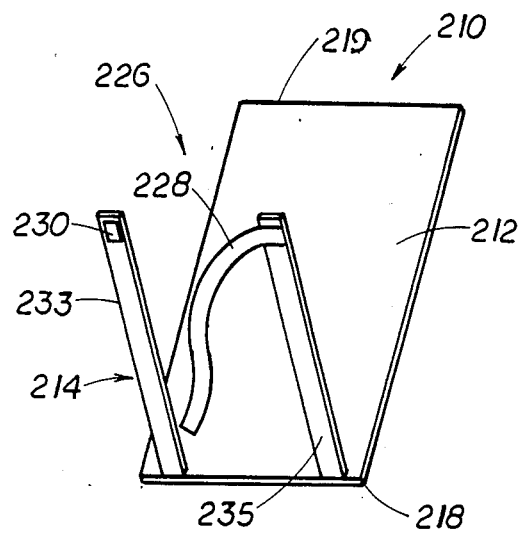
FIG. 3 is a perspective view of a further embodiment of the present invention.

Referring now to FIG. 3, there is shown another embodiment of a face and eye shield device, generally denoted as the numeral 210, of the present invention.

As shown, the face and eye shield device 210 includes a transparent face shielding panel 212 and supporting means, generally denoted as the numeral 214, for supporting the face shielding panel 212 at the wearer's chest and holding the face shielding panel 212 in front of and spaced outwardly from the wearer's face as shown in FIG. 5.

The supporting means 214 is shown as a pair of spaced apart rigid straps 233 and 235 joined at their lower ends to the face shield panel 212 proximate the lower edge 218 of the face shield panel 212 and extending upwardly therefrom. The straps 233 and 235 are adapted to lay on the wearer's chest and should be spaced apart by an appropriate distance wider than the wearer's neck. The rigid supporting straps 233 and 235 each cooperate with the face shielding panel 212 to define an equal acute included angle between the support strap 233 and 235 and face shielding panel 212.

The face shield panel 212 has a larger height dimension measured from the lower edge 218 to the top edge 219 than the length of the straps 233 and 235 as measured from lower strap ends attached to the face shield panel and the top distal ends of the straps 233 and 235.

The face and eye shield device 210 further includes means, generally denoted as the numeral 226, for suspending the face shield device 210 from the wearer's neck. As shown, the suspending means 226 is a flexible band 228 connected to the top distal ends of the rigid supporting straps 233 and 235 adapted to fit around the wearer's neck. Toward this objective, the flexible neck band 228 is attached at one end to one of the supporting straps 233. A neck band fastener 230 is attached to the other fastener 230 which, in turn, is attached to the other one of the supporting straps 235. The free end of the neck band 228 can be adjustably connected to the fastener 230 when the neck band 228 has been located across the wearer's neck.

Figure 4:
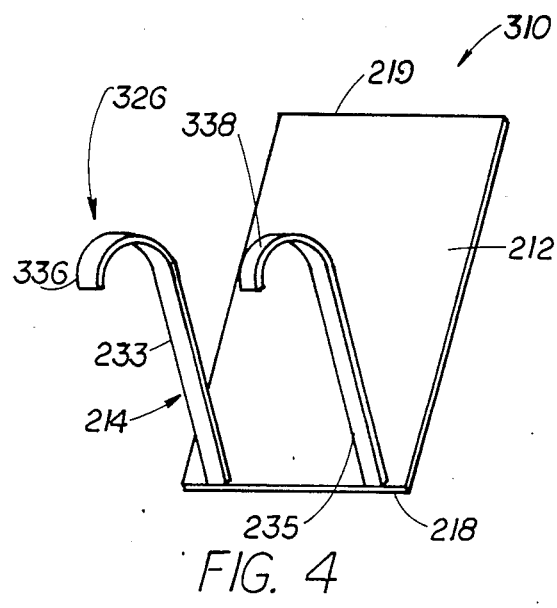
FIG. 4 is a perspective view of yet another embodiment of the present invention.

With reference to FIG. 4, there is illustrated a somewhat different embodiment of a face and eye shield device, generally denoted as the numeral 310, of the present invention. The face and eye shield 310 is identical to the face and eye shield 210 of FIG. 3 in every respect except for the suspending means, generally denoted as the numeral 326. Therefore, all of the features in common with the eye shield 210 are denoted by the same numerals, and for the sake of brevity the description of these common features will not be repeated.

The suspending means 326 of the face and eye shield device 310 suspends the face and eye shield 310 from the wearer's shoulders. Toward this objective, the suspending means 326 comprises a pair of spaced apart shoulder engaging hook members 336 and 338 at the top or distal ends of the support straps 233 and 235. Preferably, the hook members 336 and 338 are integrally formed in the top or distal end of each of the support straps 233 and 235. The shoulder engaging hook members 336 and 338 open downwardly and are sized, configured and spaced apart from each other by an appropriate distance to comfortably receive the wearer's shoulders on either side of the wearer's neck.

As an additional feature of the invention, the face shielding panel in each of the above-described embodiments may include an ultra-violet blocking material in the area of FIG. 1 denoted by the letter "A".

The foregoing detailed description is given primarily for clearness of understanding and no unnecessary limitations should be understood therefrom for modifications will become obvious to those skilled in the art upon reading this disclosure and may be made without departing from the spirit of the invention or scope of the appended claims.

What is claimed:

1. A face shield device comprising:
   a transparent planar face shielding panel;
   a planar supporting panel adapted to lay on a wearer's chest for supporting the face shielding panel at the wearer's chest and holding the face shielding panel in front of and spaced outwardly from the wearer's face and eyes only and will not extend around the sides of the wearer's head; the top edge of the supporting panel is formed with a notched out area for receiving the wearer's throat; and,
   the supporting panel and face shielding panel are joined together at their lower edges.

2. The face shield device of claim 1, wherein the supporting panel and face shielding panel cooperate to define an acute included angle therebetween with the apex of the angle being the lower jointed edges of the panels.

3. The face shield device of claim 1, further comprising means for suspending the support panel from the wearer's neck.

4. The face shield device of claim 3, wherein the suspending means comprises a flexible band connected to the support panel, the flexible band being adapted to fit around the wearer's neck.

5. The face shield device of claim 1, further comprising means for suspending the support panel from the wearer's shoulders.

6. The face shield device of claim 1, wherein the suspending means comprises a pair of spaced apart shoulder engaging hook members attached to the support panel.

7. The face shield of claim 1, wherein the face shielding panel in a preselected area, includes means to block out undesirable radiation.

8. The face shield of claim 1, wherein the face shielding panel in a preselected area includes an ultra-violet blocker.

9. A face shield device comprising:
   a transparent face shielding panel; and,
   a pair of spaced apart rigid straps joined at their lower ends to the face shield panel proximate the lower edge of the face shield panel, said joining of the straps to the lower end of the face shield panel proximate the lower edge thereof being the sole means of support between said face shield panel and said straps, the straps being adapted to lay on the wearer's chest and holding the face shielding panel in front of and spaced outwardly from the wearer's face and eyes only, said face panel will not extend around the sides of the wearer's head.

10. The face shield device of claim 9, wherein the face shield panel and each of the rigid straps cooperate to define an acute angle therebetween.

11. The face shield device of claim 10, further comprising means for suspending the spaced apart straps from the wearer's shoulders.

12. The face shield device of claim 11, wherein the suspending means comprises a shoulder engaging hook member at the top end of the rigid straps.

13. The face shield device of claim 10, further comprising means for suspending the spaced apart straps from the wearer's neck.

14. The face shield of claim 13, wherein the suspending means comprises a flexible band connected to the top ends of the rigid straps, the flexible band being adapted to fit around the wearer's neck.

* * * * *